United States Patent
Flumene et al.

[11] Patent Number: 6,022,364
[45] Date of Patent: Feb. 8, 2000

[54] DISPOSABLE SURGICAL SAFETY SCALPEL

[76] Inventors: Antonio Giovanni Flumene, Via Garavetti, 6; Giuseppe Pilo, Via Muroni, 22, both of IT-07100 Sassari, Italy

[21] Appl. No.: 09/051,548
[22] PCT Filed: Oct. 18, 1996
[86] PCT No.: PCT/EP96/04544
  § 371 Date: Apr. 7, 1998
  § 102(e) Date: Apr. 7, 1998
[87] PCT Pub. No.: WO97/15233
  PCT Pub. Date: May 1, 1997

[30] Foreign Application Priority Data

Oct. 24, 1995 [IT] Italy .................................. MI95A2194

[51] Int. Cl.[7] .................................................. A61F 9/00
[52] U.S. Cl. ......................... 606/166; 606/167; 606/170
[58] Field of Search ........................ 606/166, 167, 606/168, 189, 170, 171–185

[56] References Cited

U.S. PATENT DOCUMENTS

| | | |
|---|---|---|
| 3,905,101 | 9/1975 | Shepherd . |
| 3,906,626 | 9/1975 | Riuli . |
| 4,028,758 | 6/1977 | O'Conner . |
| 4,414,974 | 11/1983 | Dotson et al. . |
| 4,735,202 | 4/1988 | Williams . |
| 4,769,912 | 9/1988 | Davis . |
| 4,835,865 | 6/1989 | Knoop . |
| 4,858,320 | 8/1989 | Lemaire . |
| 5,116,351 | 5/1992 | Frassetti . |
| 5,207,695 | 5/1993 | Matwijcow . |
| 5,250,063 | 10/1993 | Abidin et al. . |
| 5,330,492 | 7/1994 | Haugen . |
| 5,330,493 | 7/1994 | Haining . |
| 5,330,494 | 7/1994 | van der Westhuizen et al. . |
| 5,344,424 | 9/1994 | Roberts et al. . |
| 5,364,360 | 11/1994 | Flumene et al. . |
| 5,403,337 | 4/1995 | Platts . |
| 5,417,704 | 5/1995 | Wonderley . |
| 5,431,672 | 7/1995 | Cote et al. . |

FOREIGN PATENT DOCUMENTS

| | | |
|---|---|---|
| 1002554 | 3/1991 | Belgium . |
| 0 217 638 | 4/1987 | European Pat. Off. . |
| 0 251 485 | 1/1988 | European Pat. Off. . |
| 0 612 506 | 8/1994 | European Pat. Off. . |
| 0 622 047 | 11/1994 | European Pat. Off. . |
| 37 35 294 | 4/1989 | Germany . |
| 5487 | 3/1884 | United Kingdom . |
| 1 511 889 | 5/1978 | United Kingdom . |
| WO 90/11725 | 10/1990 | WIPO . |
| WO 93/24064 | 12/1993 | WIPO . |
| WO 93/25152 | 12/1993 | WIPO . |
| WO 94/13216 | 6/1994 | WIPO . |
| WO 95/15122 | 6/1995 | WIPO . |
| WO 95/15723 | 6/1995 | WIPO . |
| WO 9524855 | 9/1995 | WIPO .................................. 606/167 |

OTHER PUBLICATIONS

Janine Jagger et al., "Suture Needle and Scalpel Blade Injuries: Frequent but Unreported", *Advances in Exposure Prevention*, vol. 1, No. 3, pp. 1 ff, Apr. 1995.

Notification of Transmittal of the International Search Report or Declaration, and attached International Search Report, Feb. 1997.

*Primary Examiner*—Michael Buiz
*Attorney, Agent, or Firm*—Merchant & Gould PC

[57] ABSTRACT

A disposable surgical safety scalpel (3) with a retractable blade that can be retracted inside a protective shell (5); return of the blade into the shell (5) is operated through an elastic return means (15), acting between a blade support (4) and said shell (5). Movement of the support (4) and thus of the blade (3) is effected by operating a pivoted button (13), facing through a window (11) of the shell (5), said pivoted button (13) being provided with an automatic lock for the blade in said retracted position in the shell (5) and a voluntary lock for the blade in the position for use.

9 Claims, 4 Drawing Sheets

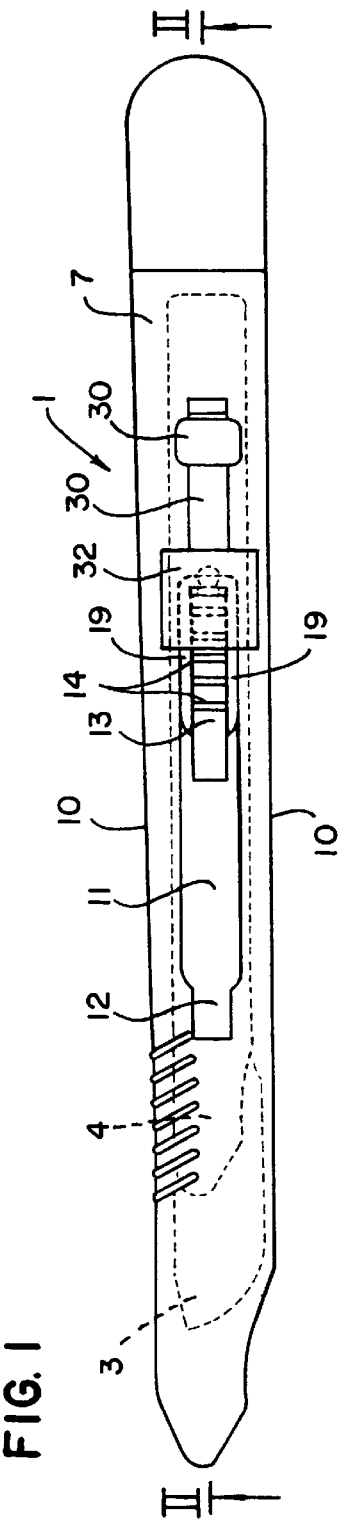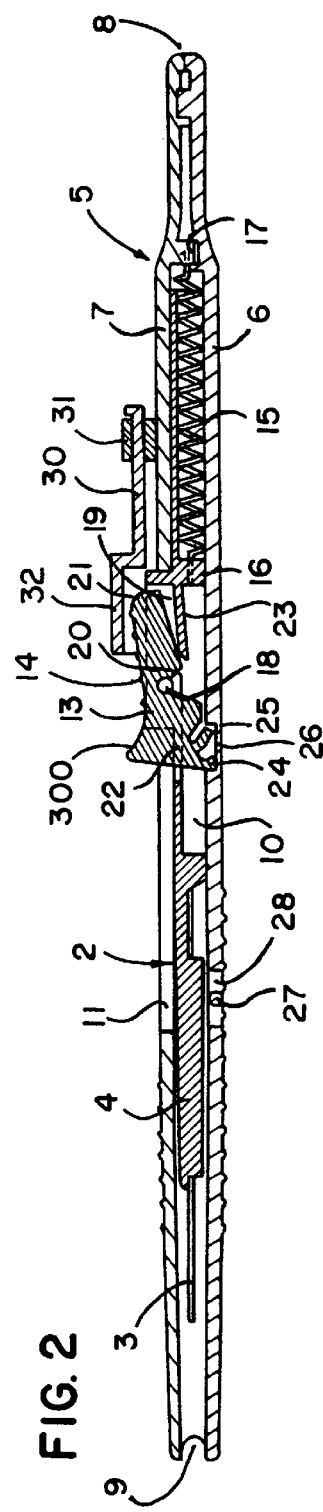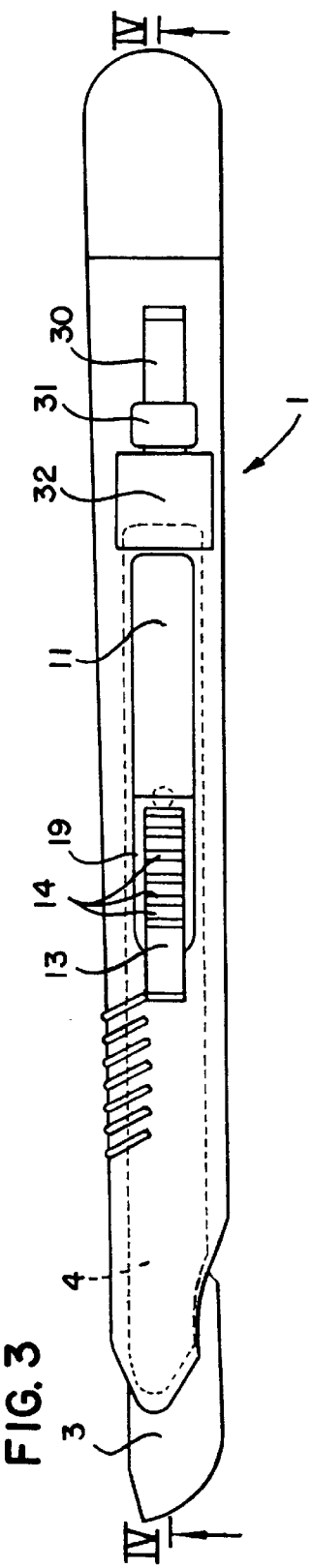

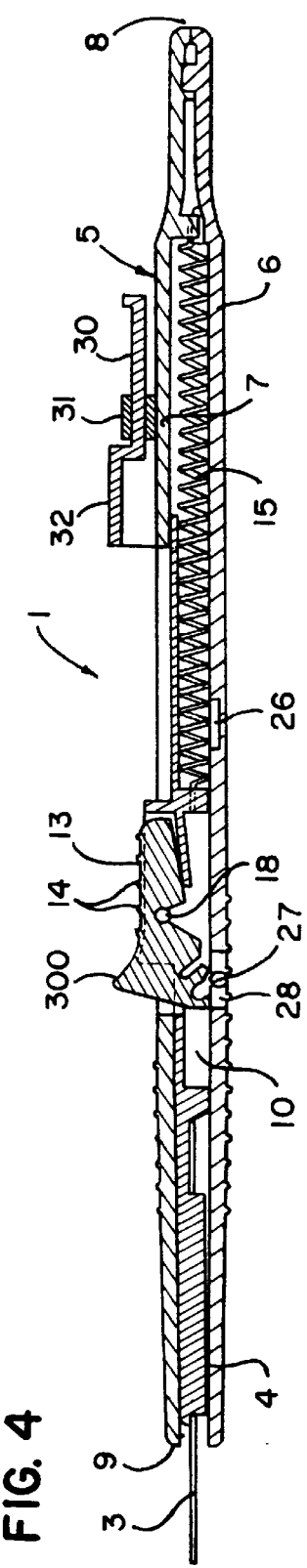
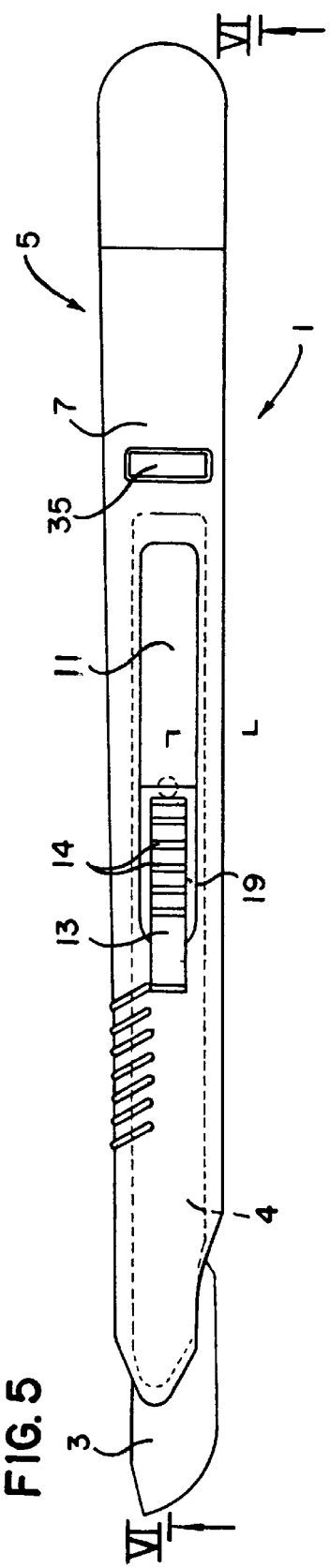
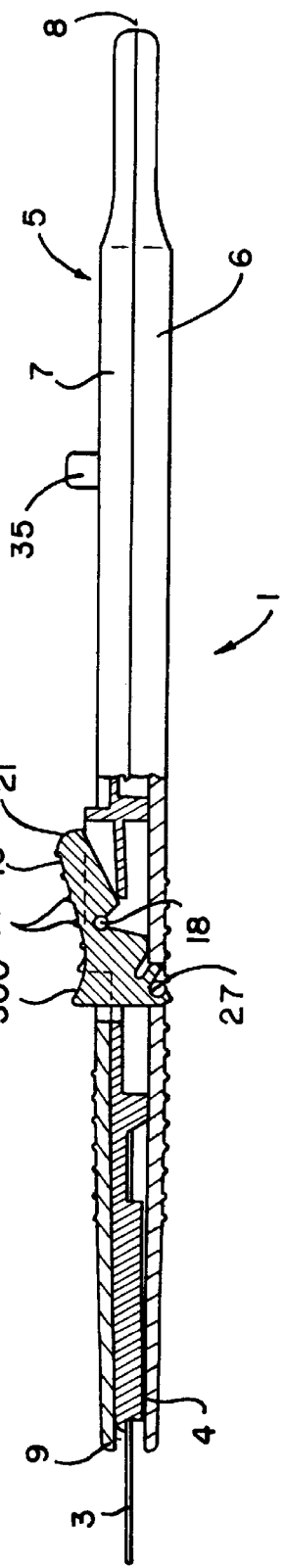

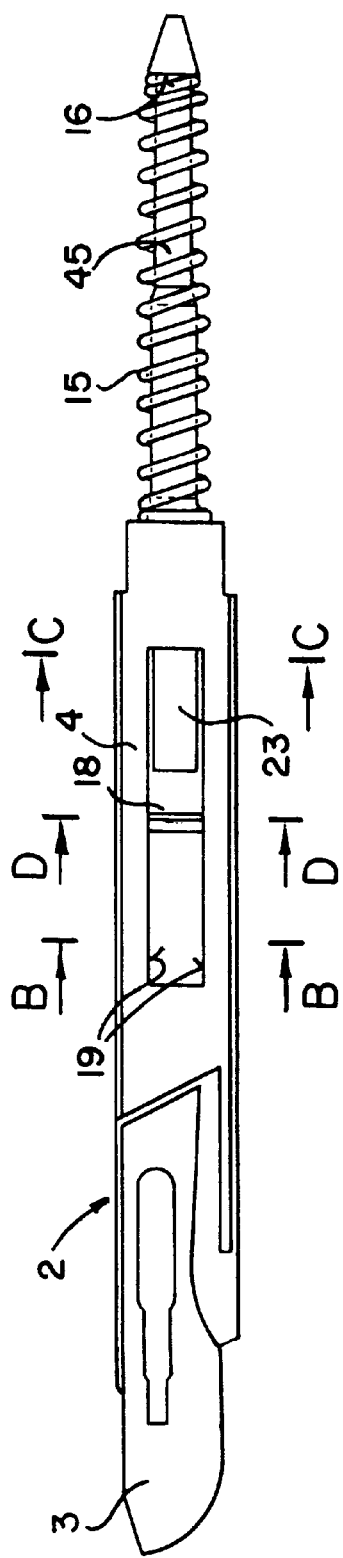
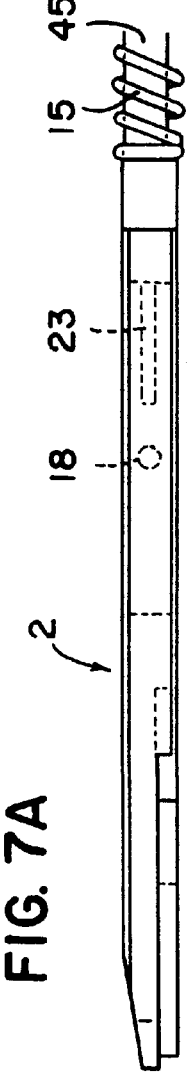
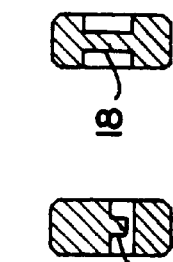
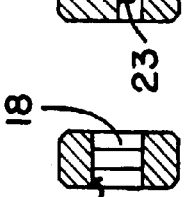
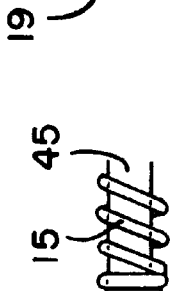
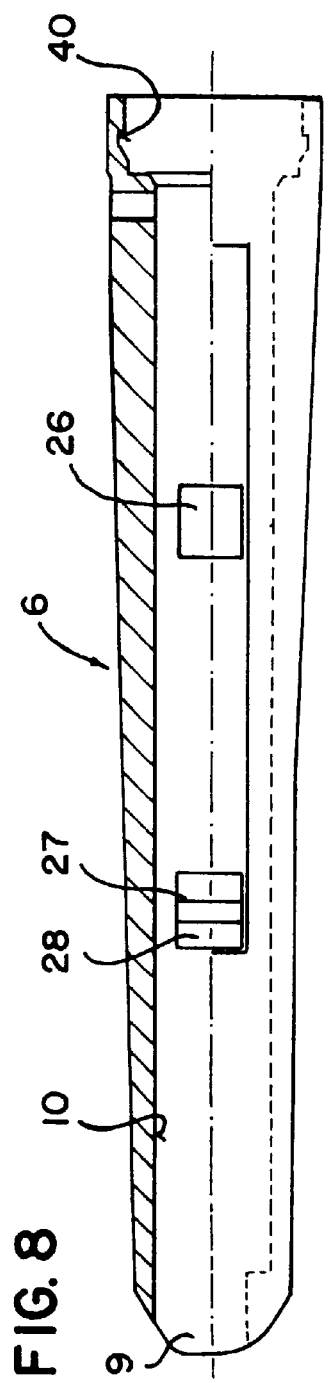

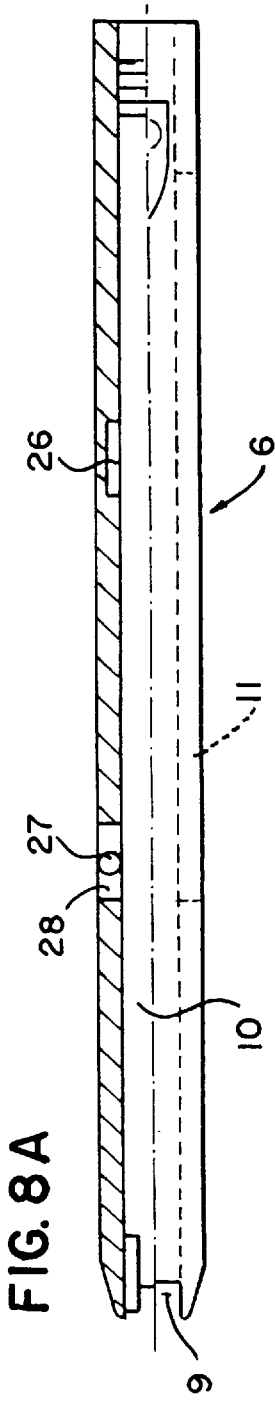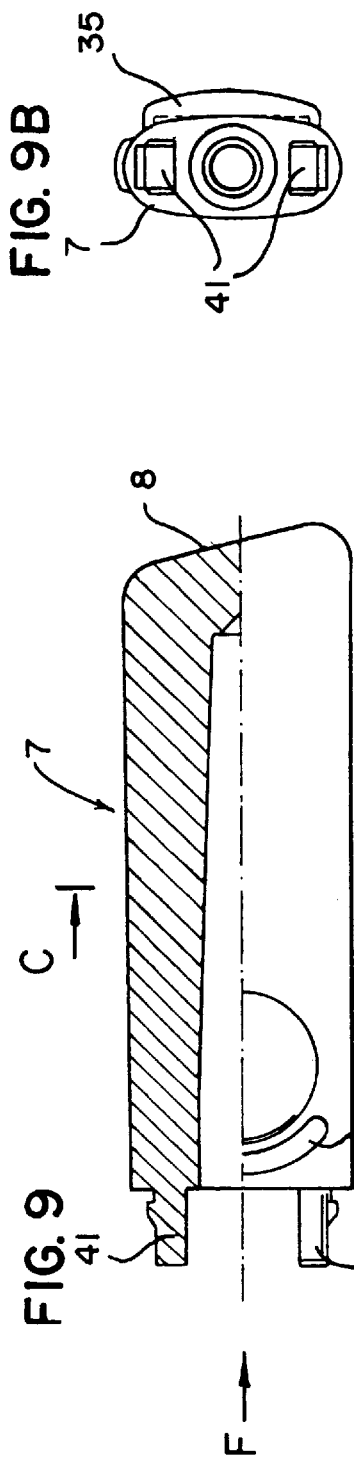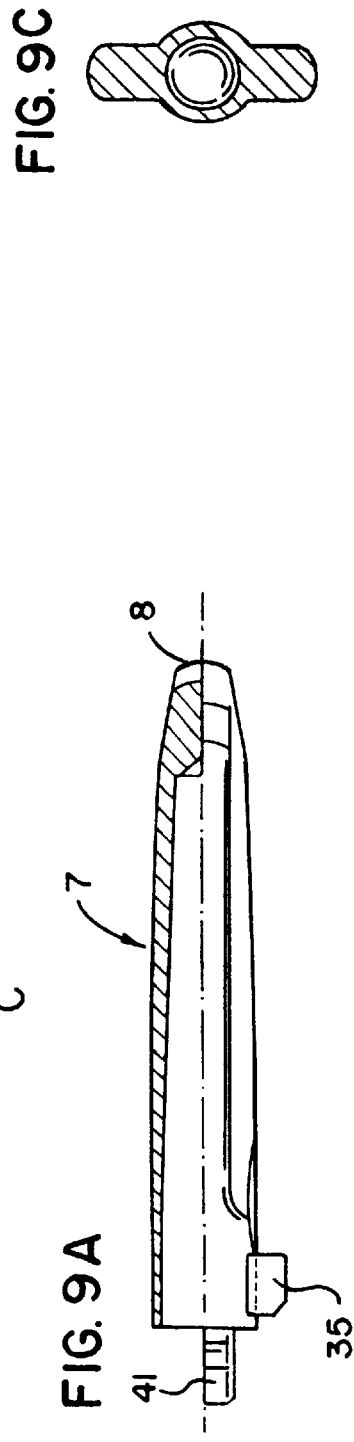

DISPOSABLE SURGICAL SAFETY SCALPEL

The present invention relates to a disposable surgical safety scalpel for medical use, having a retractable blade.

A scalpel is a highly professional surgical instrument which has been perfected over the years to such an extent that it cannot be compared to a jack knife or a cutter.

In describing the state of the art, reference can be made only from an historical viewpoint to some patents relating to knives described in the more or less recent past, whose characteristic was to have a blade that is positioned after use in a protective container.

This is the case, for example, of the following patents:

GB-5487 (LAKE), which as far back as 1884 described a knife with an extractable blade;

U.S. Pat. No. 4,028,758 (O'CONNOR), which describes a combination of a utility knife and a staple remover;

U.K. 1511889 (STEABBEN), which describes a pocket cutter with a blade that retracts but not automatically;

U.S. Pat. No. 4,769,912 (DAVIS), which describes a knife with an acceleration sensor;

U.S. Pat. No. 4,858,320 (LEMAIRE), which describes a pocket knife with retractable blade;

DE-3735294 (TEIHS), U.S. Pat. No. 4,835,865 (KNOOP) and lastly BE.1.002.554 (VAN HOOYDONCK), which describe an industrial cutter with retractable blade.

As is well known, the surgical scalpels existing on the market are of the disposable or reusable type, with a fixed or interchangeable blade, and do not normally have any protection, except for a blade protecting cap in the case of disposable scalpels, which cap is slipped off before use and could be replaced after use.

In fact the cap should never be replaced because this maneuver can cause unwelcome cuts, with the risk of transmission of diseases, including serious ones like AIDS and viral hepatitis.

The use of a barrier system, such as gloves with a steel mesh, which protect from cuts but not from stab wounds, is not well accepted because of the increased thickness and stiffness of the gloves, which leads to a loss of sensitivity.

The use of a different system, called "Magnetic Drape", which consists of a sort of magnet cloth to be placed near the operating field and to which the surgical instruments adhere through the action of a magnet, avoids the stage of passing the instruments from hand to hand, thus eliminating some wounds, i.e. those that occur during exchange of instruments between operators.

This system is poorly received by surgeons because it is essential to look away from the operating field to grasp the instrument and also because it is of no use for non-metallic objects.

The majority of accidental scalpel stab wounds or cuts occurs not so much when the surgeon makes an incision in the patient's skin or tissue as when the scalpel is passed from hand to hand by the medical operators or during disposal.

A study published in the USA in April 1995 by Dr. Janine Jagger in "Advances in exposure prevention", Volume 1 No. 3 published by "INTERNATIONAL HEALTH CARE WORKER SAFETY RESEARCH AND RESOURCE CENTER" showed that 34% of scalpel wounds occur during use of the instrument, whilst the remaining 39% and 27%, respectively, take place when the scalpel is passed from hand to hand by operators and during removal-replacement-disposal of the blade.

From these data it emerges that, overall, scalpels with an exposed blade or an interchangeable blade are responsible for 66% of cut wounds that occur among medical operators before, during and after use of the instrument.

It is for this reason that all scalpels with an exposed blade, such as those currently on the market must be considered dangerous, as well as those with an interchangeable blade, such as those forming the object of the following patents:

PCT-WO 90/11725 (DOLGIN), which describes a metal scalpel with a mobile guard, with no automatic return and requiring replacement of the blade;

U.S. Pat. No. 5,250,063 (ABIDIN), which describes a metal scalpel with a mobile guard and an interchangeable blade;

PCT-WO 94/13216 (WERNER), which describes a metal scalpel with a voluntarily or automatically retracting blade that is extremely dangerous in that pressure exerted on the rear part causes an accidental forward movement of the blade, is difficult to construct and also has an interchangeable blade;

PCT-WO 95/15723 (GHARIBIAN), which describes a scalpel with a mobile guard and interchangeable blade without any locking system between the cap and the blade holder, making it difficult to use and dangerous;

PCT-WO 93/24064 (NEWMAN P. H.) and U.S. Pat. No. 5,403,337 (PLATTS) which describe a disposable scalpel with a blade that can be changed during the surgical procedure, without foreseeing any protection for used blades.

Changing of the blade is in fact the weak point of any instrument, even those considered safe, because handling necessarily leads to an increased risk of accidental wounds.

In the analysis of the state of the art it can be seen that as time went on inventors refined the idea of a safe scalpel to meet the need for protection required by surgeons.

Starting from mobile blade protection systems without automatic return, such as, for example, those described in patents:

U.S. Pat. No. 3,905,101 (SHEPHERD), U.S. Pat. No. 3,906,626 (RIULI), U.S. Pat. No. 4,414,974 (DOTSON), EP-0 251 485 (GORDY), U.S. Pat. No. 4,735,202 (WILLIAMS), EP-0 612 506 (NEWMAN C. D.), whose main defects lie in the need to use both hands to set up or to protect the instrument and the necessity to remember to cover the blade each time it is passed from hand to hand, systems have been designed with a mobile blade guard that can be moved with only one hand, but still without automatic return of the cap, such as those described in patents:

PCT-WO 90/11725 (DOLGIN), U.S. Pat. No. 5,250,063 (ABIDIN), U.S. Pat. No. 5,417,704 (WONDERLEY), PCT-WO 95/15723 (GHARIBIAN), in which advancement and retraction of the protective cap is carried out with one hand and must be intentional on the part of the operator.

Again with regard to mobile guard, the following patents must be considered separately:

U.S. Pat. No. 5,330,492 (HAUGEN), which describes a scalpel with a guard that can be moved by means of a push-button, which when pressed causes the protective cap to retract, uncovering the blade, and when released unintentionally causes the opposite effect; this instrument must be grasped in a an unnatural way, does not offer guarantees of safety because the push-button protrudes excessively and in addition, because of its excessive height, does not allow a correct cutting angle on the skin surface;

U.S. Pat. No. 5,330,494 (VAN DER WESTHUIZEN), which describes a guard that can move transversely to the blade, constituting a danger not only for the operators, because pressure exerted casually on the lower edge of the cap causes uncovering of the blade with a high risk of wounds, but also for patients since the cutting force cannot be regulated.

More recently different systems have been proposed, such as, for example, that in U.S. Pat. No. 5,116,351 (FRASSETTI), which describes a mobile blade mechanism, with automatic return of the blade to the protected position and with the possibility of voluntary locking, but is basically awkward because it obliges the operator to work in an unnatural position, that is with the finger exerting a certain pressure on the upper edge of the blade and with the blade partly covered by the protection system; and that of U.S. Pat. No. 5,207,696 (MATWIJCOW), which describes a scalpel with a retractable blade and mobile guard, but which seems too bulky and therefore awkward and has no automatic involuntary return of the blade to the covered position.

A further development in the design of these instruments has come about with a concept that foresees the possibility of extracting the blade from the handle. This is probably the idea that holds most advantages because it offers interesting solutions to the problems described up to now, although each of the ideas proposed gives rise to some considerations as regards their practical operation.

A first proposal for a retractable blade is presented in:

EP-0 217 638 (DESATNICK), which describes an instrument for closed cavity surgery, with a small retractable blade, without automatic return, not disposable, therefore dangerous during blade changes, and not suitable for skin incisions;

PCT-WO 93/24064 (NEWMAN P. H.), which describes a scalpel with locking of the exposed blade, which is very difficult to set up, with voluntary return, with the risk of the blade holder with the blade coming out accidentally from the rear part of the cover, without any protection against an accidental forward movement of the blade and with the possibility of replacing the blades during a surgical procedure, an operation which seems dangerous because the exposed blade is handled;

U.S. Pat. No. 5,330,493 (HAINING) which describes a disposable scalpel with a retractable blade, without automatic return of the blade to the resting position, with a button for forward movement of the blade that is situated on its upper edge and is therefore awkward to slide, and with a permanent end-of-use lock, which seems superfluous and could sometimes be applied accidentally, thus making it impossible to use the instrument;

PCT-WO-94/13216 (WERNER), which describes a metal scalpel with voluntary automatic retraction of the blade that is extremely dangerous because if pressure exerted on its rear part causes an accidental unintentional forward movement of the blade, that is difficult to construct and also has an interchangeable blade;

PCT-WO-95/15122 (WERNER) is different from the preceeding one for the use of a different system of locking of the blade in an operative position.

U.S. Pat. No. 5,344,424 (ROBERTS) which presents a disposable scalpel with voluntary retraction, with three locking positions, i.e. an operative or set up position, an inoperative position and a safety position, where the only innovation appears to be the internal safety device, but which is difficult to handle and dangerous because the blade advance system protrudes too far;

EP-0 622 047 (DERBYSHIRE), which describes an original blade advance system in which pressure is exerted on a flexible container (balloon), with automatic spring-operated return, with the defect that seeing the blade retract each time pressure is exerted on skin or tissues because of the intrinsic elasticity of the balloon itself, and the blade can accidentally move forward through unintentional pressure exerted by other instruments or hands;

U.S. Pat. No. 5,403,337 (PLATTS), which describes a scalpel wholly similar to the one described in PCT-WO 93/24064 (NEWMAN P. H.), criticizing it as awkward and dangerous and adding its own small modification to eliminate these defects, but making it more difficult to set up with only one hand (the rear part of the handle has been widened to allow for positioning of two stops) and still foreseeing blade changes during the surgical procedure, which continues to represent a hazard;

U.S. Pat. No. 5,431,672 (COTE), which presents a scalpel with automatic voluntary return of the blade with an additional internal lock, which could be accidentally applied during surgical procedures, forcing the medical staff to use a new scalpel; the voluntary locking of the blade in the operative position is complicated and unconfortable to be engaged and disengaged and require the use of both the hands.

PCT-WO-95/24855 (DILLON), which shows a scalpel with automatic, voluntary blade return, with an unsafe stopping system for the exposed blade and with locking devices not better identified to avoid re-use;

PCT-WO 93/25152 (FLUMENE et al.), which presents a disposable scalpel with rear lock to prevent any accidental forward movement of the blade, with easy blade exposure, without any locking in the operative or set up position of the blade, so as to have automatic, involuntary return and locking in the resting position; moreover, a particular characteristic is the possibility of graduating extraction of the blade according to the type of incision, always acting on the instrument in a comfortable, ergonomic position; the only drawback to be noted is that since it does not have a forward lock use of this instrument is rather awkward in some operating conditions, so the presence of a stop device for the blade in operative position could be desirable in some circumstances.

The aim of this invention is, therefore, to solve some of the problems posed by the prior art.

In particular, an aim of the invention is to provide a scalpel that is safe when passed among the operators, protected during transport and disposal of used materials and offers different possibilities of use, so that it is accepted by virtually all users, irrespective of their preferences for handling of the instrument.

Another aim of the invention is to provide safety locks for the blade that can easily be removed by moving one finger of the hand holding the scalpel, which is the same finger used to advance the blade.

Yet another aim of the invention is to provide a protected scalpel of the above type that is easy to construct, automatically assemblable and economical.

A surgical safety scalpel in accordance with the invention is characterized by the characteristics listed in appended independent claim 1.

Advantageous embodiments of the invention are described in the dependent claims.

Essentially, the scalpel according to the invention is provided with a voluntary locking means for intentionally locking the blade in position for use, which the operator can operate or not, depending on how he prefers to work.

If this locking means is operated, it must be disabled after use to allow return of the blade.

This manoeuvre is extremely simple, however, and does not require particular care on the part of the user.

An advantage of the present invention lies in the presence of an automatic lock which operates at the end of a run retraction of the blade, thus avoiding an accidental emerging of the same.

Another advantage of the present invention therefore lies in the fact that the manoeuvres made on the scalpel (releasing the rear lock—advancing the blade—inserting and releasing the front lock when required) are effected by means of a single finger of a same hand, keeping the scalpel in its correct use position and leaving the other hand free to make another action.

The use of a single hand and the fact that there is no necessity to take the eyes off the operation field make it possible for the surgeon's procedure not to be modified, representing therefore a further reason why this safe device can be well accepted by the medical class.

Further characteristics of the invention will be made clearer from the detailed description given below, referring to, one of its purely exemplary and therefore non-limiting embodiments, illustrated in the appended drawings, in which:

FIG. 1 is a top plan view of a scalpel according to the invention, in a first embodiment, with the blade retracted inside the shell, in an inoperative position;

FIG. 2 is a median section, taken along the line II—II in FIG. 1;

FIG. 3 is a top plan view of the scalpel in FIG. 1, with the blade in position for use;

FIG. 4 is a median section taken along the line IV—IV in FIG. 3, and shows that the voluntary blade lock has not been applied;

FIG. 5 is a top plan view of the scalpel in FIG. 1, with the blade extracted, in the operating position, as in FIG. 3;

FIG. 6 is a median section taken along the line VI—VI in FIG. 5, and shows voluntary locking of the blade in said operating position;

FIG. 7 is a plan view of a support-slider of a scalpel in accordance with an embodiment of the invention;

FIG. 7A is a side view of the support in FIG. 7;

FIGS. 7B, 7C, 7D are sections taken along the planes B—B, C—C and D—D, respectively, in FIG. 7;

FIG. 8 is a plan view, in partial section, of a half-shell able to accommodate the support in FIG. 7;

FIG. 8A is a side view, in partial section, of the half-shell in FIG. 8;

FIG. 9 is a plan view, in partial section, of a second half-shell, suitable for coupling to the half-shell in FIG. 8;

FIG. 9A is a part-sectional side view of the half-shell in FIG. 9;

FIG. 9B is a front view taken in the direction of the arrow F in FIG. 9;

FIG. 9C is a section taken along the plane C—C in FIG. 9.

With reference to the appended figures, and for now to FIGS. 1–6 in particular, a safety scalpel according to a first embodiment of the invention has been indicated as whole with reference number 1. It comprises a scalpel proper 2, consisting of a blade 3 and an elongated support 4 and a shell or outer case 5, acting as a handle, made in two halves or half-shells 6, 7, joined together by mortising or assembled in another way, for example by welding.

The scalpel 2 is housed inside the shell 5, which has one end 8 closed and the opposite end 9 open, and has the possibility of sliding longitudinally, in such a way that the blade 3 can be brought from a resting or inoperative position in which it is housed completely inside the shell 5 (FIGS. 1 and 2), to an operative position or position for use, in which it projects from the open end 9 of the shell 5 (FIGS. 3–6).

The elongated support 4 of the blade 3 acts as a slider and is guided between the side walls 10 of the shell 5. In the upper half or half-shell 7 a longitudinal aperture or window 11 is foreseen, with a substantially rectangular shape, with a narrowing 12 at the front, on the side where the blade 3 is positioned. A push-button or pivoted button 13 of the support 4 appears in the window 11, protruding only slightly from the window 11, the operator being able to operate said button with one finger to cause the support-slider 4 to slide. To make the button easier to grip, normally with the thumb, transverse ribs 14 are provided on it.

The support 4 is held in its retracted position when it is housed inside the shell 5 by an elastic means, in particular by a tensile spring 15 operating between a small pin 16 projecting downward from the support 4 and a small pin 17 projecting downward from the upper half-shell 7, in the vicinity of the closed end 8 of the shell 5.

The pivoted or oscillating button 13 pivots on a pin 18, disposed transversely to the support 4, between a pair of vertical, longitudinal, opposite facing side walls 19.

To permit automatic assembly, the button 13 has an open bottom housing 20 that allows the button 13 to be forcedly mounted on pin 18 from the outside through said window 11 provided in the half-shell 7.

The pivoted button 13 is so shaped that its rear part 21 (with reference to the appended figures), that is the part facing, toward the closed end 8 of the shell 5, has a lower height than the front part 22, and is situated above an elastic tongue 23 of the support 4, said tongue being able to bend in the plane of oscillation of the pivoted button 13.

The front end 22 of the button 13, on the other hand, has an inner or lower protrusion 24, at which a circular seat 25 is provided, open at the bottom.

Said lower protrusion 24 of the pivoted button 13 is able to fit in a seat 26 provided on the inside of the lower half-shell 6 of the shell 5, when the blade is in a retracted position inside the shell, and therefore forms a lock for the blade itself, preventing the blade from emerging accidentally.

A circular open housing 25 provided below the button 13, on the other hand, is such as to engage a transversal pin 27 provided in an opening 28 in the lower half-shell 6 when the user voluntarily operates the button 13, thus forming a voluntary lock for the blade in conditions of use.

FIGS. 1 and 6 also show a further rear safety device for the blade, that is able to prevent the blade from accidentally emerging if involuntary pressure is exerted on the rear part of the button 13, causing disengagement of the protrusion 24 from the seat 26. This device, in the embodiment illustrated in FIGS. 1 to 4, comprises a slide 30, sliding longitudinally in a guide bridge 31, and having at its front a cover member 32 able to be positioned on the back part of the pivoted button 13 (see FIGS. 1 and 2), preventing any pressure on the button itself. Member 32 is advantageously higher than the guide bridge 31 for the slide 30, so that the safety device intervenes automatically when the scalpel is passed from hand to hand, should part of the user's hand be directed towards the button 13.

A simpler solution, though with a lower degree of safety, consists in providing a small projecting wall 35, shown schematically in FIGS. 5 and 6, situated upstream of the window 11 and forming an obstacle for the finger, such as to prevent contact with the button 13.

The scalpel according to the invention works as follows.

When the scalpel is not in use, the spring 15 holds the support 4 in a retracted position inside the shell 5, as shown in FIGS. 1 and 2. In this condition, the elastic tongue 23 pushes the back part 21 of the horizontally pivoted button 13 upward, causing the front protrusion 24 to enter the seat 26 provided in the half-shell 6, thus forming a lock for the blade 3 in the retracted position, which prevents it from accidentally emerging. This lock is of the unintentional type, i.e. it intervenes automatically, irrespective of whether the user intends to operate it.

Starting from the position shown in FIGS. 1 and 2, in order to use the scalpel it is first necessary to move the safety cover member backwards, with the thumb of one hand, if said safety member is in the active position, as shown in FIGS. 1 and 2. It is therefore sufficient to exert a light pressure on the rear part 21 of the pivoted button 13, with the same thumb, and push the button 13 forwards, in the direction of the open end 9 of the shell 5, so as to cause the blade 3 to emerge, as shown in FIGS. 3 and 4. In this condition, the scalpel is ready for use, without the blade being locked in this position, locking which takes place only through a voluntary action on the part of the surgeon, as will be seen with reference to FIGS. 5 and 6.

Remaining within the context of FIGS. 3 and 4, after use of the instrument, simply releasing the button 13 causes the blade to return automatically inside the shell 5, through the action of return spring 15, with consequent automatic locking, through engagement of the protrusion 24 of the button 13 in the seat 26 of the half-shell 6.

Use of the scalpel shown in FIGS. 3 and 4, without locking of the blade, is suitable for that group of users that prefers automatic return of the blade 3 after use, without any manoeuvre having to be carried out. An alternative to use of the scalpel according to the invention is shown in FIGS. 5 and 6, in which locking of the blade has taken place, through a voluntary action on the part of the user, by means of engagement of the housing 25 of the button 13 with the pin 27 provided in the half-shell 6.

After use of the scalpel in the position shown in FIGS. 5 and 6, pressure must be exerted on the rear part 21 of the pivoted button 13, to cause unlocking of the blade and therefore its return inside the shell 5.

The shell 5, the support 4 and the pivoted button 13 are advantageously made of plastic whilst the spring 15 can be of plastic, metal, rubber or with an air or gas system or the like.

It is also obvious that the blade 3 can have any shape, depending upon its use, without the characteristics of the scalpel according to the invention undergoing any changes.

To aid voluntary locking of the blade in the position for use (FIGS. 5 and 6) the horizontally hinged button 13 has a raised part 300 at the front, which facilitates the lowering action to cause engagement of its housing 25 with the pin 27.

FIGS. 7–9 show a different embodiment of the scalpel according to the invention, which differs from that illustrated previously in that the two halves or half-shells 6, 7 of the shell 5, instead of being assembled along a longitudinal plane, are assembled along a transversal plane. In this embodiment, the elements that are the same or corresponding are marked with the same reference numbers as those used in relation to FIGS. 1–6, and will not be further described. In particular, the support-slider 4 of the blade and the locking means for said support-slider by means of the pivoted button 13 remain unchanged.

Therefore, only the parts that differ from the preceding embodiment will be described briefly below.

The half-shells 6 and 7, respectively, form a hollow body and a covering cap of the shell 5, and are assembled together by means of seats 40 and flexible tongues 41, respectively.

Before the shell is closed, the support-slider 4 is inserted axially from the rear of the half-shell 6. At the back of the support-slider a rod- or stem-shaped protrusion 45 is provided which is inserted in the hollow of the cap 7. Around the stem 45 a pressure spring 15 is arranged, between a widened terminal pin 16 of the stem 45, on one hand, and an inner abutment of the shell 5 in the assembled condition, on the other.

In FIGS. 7–9, an arched raised wall 35, similar to that shown in FIGS. 5 and 6, has been indicated as an additional safety device against unintentional operation of the button 13 (FIGS. 9, 9A, 9B). It is obvious, however, that the additional safety means can consist of the cover means shown in FIGS. 1–4.

We claim:

1. A disposable surgical safety scalpel comprising a blade, fixed at one end to an elongated support, sliding longitudinally inside a protective shell, to bring said blade from a retracted inoperative position, in which it is housed inside said shell, to an exposed operative position, through the action of an operator who acts on a button of the support inserted in a window of said shell, an elastic return means to bring said blade back into the retracted inoperative position, said return means acting between said support and said shell, said button co-operating with said shell to provide automatic locking of the blade in said retracted inoperative position, wherein said button is a pivoted button, pivotally mounted on said support, having means that can be brought into engagement, upon a voluntary pressing action by the user on said button, with a corresponding means provided in said shell, when said blade is in said exposed operative position, wherein said means provided inside said pivoting button, is an open housing, and said corresponding means provided in said shell is a pin.

2. A disposable surgical safety scalpel comprising a blade, fixed at one end to an elongated support, sliding longitudinally inside a protective shell, to bring said blade from a retracted inoperative position, in which it is housed inside said shell, to an exposed operative position, through the action of an operator who acts on a button of the support inserted in a window of said shell, an elastic return means to bring said blade back into the retracted inoperative position, said return means acting between said support and said shell, said button co-operating with said shell to provide automatic locking of the blade in said retracted inoperative position, wherein said button is a pivoted button, pivotally mounted on said support, having means that can be brought into engagement, upon a voluntary pressing action by the user on said button, with a corresponding means provided in said shell, when said blade is in said exposed operative position, wherein said pivoted button is pushed by an elastic tongue of the support against the inner wall of said shell opposite that having said window and said pivoted button has an inner protrusion that engages with a corresponding seat made inside said shell, under the action of said elastic tongue with said blade is in said retracted inoperative position.

3. A disposable surgical safety scalpel comprising a blade, fixed at one end to an elongated support, sliding longitudinally inside a protective shell, to bring said blade from a retracted inoperative position, in which it is housed inside said shell, to an exposed operative position, through the action of an operator who acts on a button of the support inserted in a window of said shell, an elastic return means to bring said blade back into the retracted inoperative position, said return means acting between said support and said shell, said button co-operating with said shell to provide automatic locking of the blade in said retracted inoperative position, wherein said button is a pivoted button, pivotally mounted on said support, having means that can be brought into engagement, upon a voluntary pressing action by the user on said button, with a corresponding means provided in said shell, when said blade is in said exposed operative position, further comprising an additional safety means against accidental emergence of said blade, comprising a cover means that can be brought, by means of a longitudinally sliding slide, to cover said pivoted button at least partly.

4. A scalpel according to claim 1 further comprising an additional safety means against accidental emergence of said blade, comprising a cover means that can be brought, by means of a longitudinally sliding slide, to cover said pivoted button at least partly.

5. A scalpel according to claim 2 further comprising an additional safety means against accidental emergence of said blade, comprising a cover means that can be brought, by means of a longitudinally sliding slide, to cover said pivoted button at least partly.

6. A scalpel according to claim 1, wherein a safety means is provided against accidental operation of said pivoted button, consisting of a small raised wall situated upstream of said window of the case or said shell.

7. A scalpel according to claim 1, wherein said shell is made in two halves or half-shells assembled together.

8. A scalpel according to claim 7, in which said half-shells are assembled along a longitudinal plane of said scalpel.

9. A scalpel according to claim 7, in which said half-shells are assembled along a transversal plane of said scalpel.

* * * * *